United States Patent [19]
Nielsen et al.

[11] Patent Number: 5,589,331
[45] Date of Patent: Dec. 31, 1996

[54] METHOD FOR DETECTING ABNORMAL SEROTONERGIC FUNCTION

[75] Inventors: David A. Nielsen, Kensington; David Goldman, Potomac; Markku Linnoila, Bethesda, all of Md.; Matti Virkkunen, Helsinki, Finland

[73] Assignee: The United States of America as represented by the Department of Health and Human Services, Washington, D.C.

[21] Appl. No.: 125,628

[22] Filed: Sep. 22, 1993

Related U.S. Application Data

[63] Continuation-in-part of Ser. No. 873,913, Apr. 24, 1992, abandoned.

[51] Int. Cl.$^6$ .............................. C12Q 1/68; C07H 21/04; C12P 19/34
[52] U.S. Cl. ....................... 435/6; 536/24.33; 536/23.2; 435/91.2
[58] Field of Search ............................... 435/6, 193, 91.2; 536/23.2, 24.33

[56] References Cited

FOREIGN PATENT DOCUMENTS

WO93/22458  11/1993  WIPO .

OTHER PUBLICATIONS

Nielsen et al., Am J. Hum. Genet. 51(6): 1366–1371 (Dec. 1992).
Ainsworth et al., "Diagnostic single strand conformational polymorphism, (SSCP): a simplified non–radioisotopic method as applied to a Tay–Sachs B1 variant," *Nucleic Acids Research*, 19(2): 405–406 (1991).
Arato et al., "Serotonin dysregulation in suicide," *Royal Society of Medicine Services International Congress and Symposium*, Series No. 165, pp. 41–46 (1991).
Asberg et al., "5–HIAA in the Cerebrospinal Fluid," *Arch Gen Psychiatry*, 33: 1193–1197 (1976).
Ballenger et al., "Alcohol and Central Serotonin Metabolism in Man," *Arch Gen Psychiatry*, 36:224–227 (1979).
Boularand et al., "Complete coding sequence of human tryptophan hydroxylase," *Nucleic Acids Research*, 18 (14): 4257 (1990).
Craig et al., "Localization of human tryptophan hydroxylase (TPH) to chromosome 11p15.5→p14 by in situ hybridization," *Cytoenetics and Cell Genetics*, 56 (3–4):157–159 (1991).
Grenett et al., "Full–length cDNA for rabbit tryptophan hydroxylase: Functional domains and evoluation of Aromatic Amino acid hydroxylases," *Proc. natl. Acad. Sci. USA*, 84:5530–5534 (1987).
Kim et al., "Molecular cloning and characterization of cDNA encoding tryptophan hydroxylase from rat central serotonergic neurons," *Molecular Brain Research*, 9:277–283 (1991).
Kovar et al., "Two dimensional single–strand conformation polymorphism analysis: a useful tool for the detection of mutations in long DNA fragments," *Nucleic Acids Research*, 19 (13): 3507–3510 (1991).
Roy et al., "Cerebrospinal fluid monoamine metabolites in alcoholic patients who attempt suicide," *Acta Psychiatr Scand*, 81:58–61 (1989).

(List continued on next page.)

*Primary Examiner*—Stephanie W. Zitomer
*Attorney, Agent, or Firm*—Townsend and Townsend and Crew LLP

[57] ABSTRACT

A method of detecting abnormal serotonergic function in an impulsive human subject is disclosed. The method comprises detecting an L allele of a gene encoding tryptophan hydroxylase. The invention also includes an isolated nucleic acid having a sequence specific to an L allele of a gene encoding tryptophan hydroxylase. The nucleic acid may migrate in a denaturing gel at the same rate as a second nucleic acid specific to a corresponding region of a U allele of a gene encoding tryptophan hydroxylase, and migrate in a nondenaturing gel at a rate about 1.02 times the migration rate of the second nucleic acid.

13 Claims, 7 Drawing Sheets

OTHER PUBLICATIONS

Lester, "Biochemical correlates of suicidal behavior in arsonists," *Psychological Reports*, 64:258 (1989).

Linnoila et al., "Low cerebrospinal fluid 5–hydroxyindoleacetic acid concentration differentiates impulsive from nonimpulsive violent behavior," *Life Sciences*, 33:2609–2614 (1983).

Lopez–Ibor Jr., et al., "Serotonin, impulsiveness and aggression in humans," *Royal Society of Medicine Services International Congress and Symposium*, Series No. 165, pp. 35–40 (1991).

Mann et al., "Increased Serotonin$_2$ and β–Adrenergic Receptor Binding in the Frontal Cortices of Suicide Victims," *Arch Gen Psychiatry*, 43:954–959 (1986).

Oreland et al., "Platelet MAO Activity and Monoamine Metabolites in Cerebrospinal Fluid in Depressed and Suicidal Patients and in Healthy Controls," *Psychiatry Research*, 4: 21–29 (1981).

Orita et al., "Rapid and Sensitive Detection of Point Mutations and DNA Polymorphisms Using the Polymerase Chain Reaction," *Genomics*, 5:874–879 (1989).

Woodcock in Restak, ed. "A Neuropsychiatric Approach to Impulse Disorders," *Psychiatric Clinics of North America*, 9 (2): 341–352 (1986).

Roy et al., "Serotonin in Suicide, Violence, and Alcoholism," *Serotonin in Major Psychiatric Disorders*, pp. 187–208 (1990) Cocaro et al. ed.

Soubrie et al., "Reconciling the role of central serotonin neurons in human and animal behavior," *The Behavioral and Brain Sciences*, 9 (2):319–364 (1986).

Stoll et al., "Isolation and Structural Characterization of the Murine Tryptophan Hydroxylase Gene," *Journal of Neuroscience Research*, 28:457–465 (1991).

Traskman et al., "Monoamine Metabolites in CSF and Suicidal Behavior," *Arch Gen Psychiatry*, 38:631–636 (1981).

Virkkunen et al., "Cerebrospinal Fluid Monoamine Metabolite Levels in Male Arsonists," *Arch Gen Psychiatry*, 44:241–247 (1987).

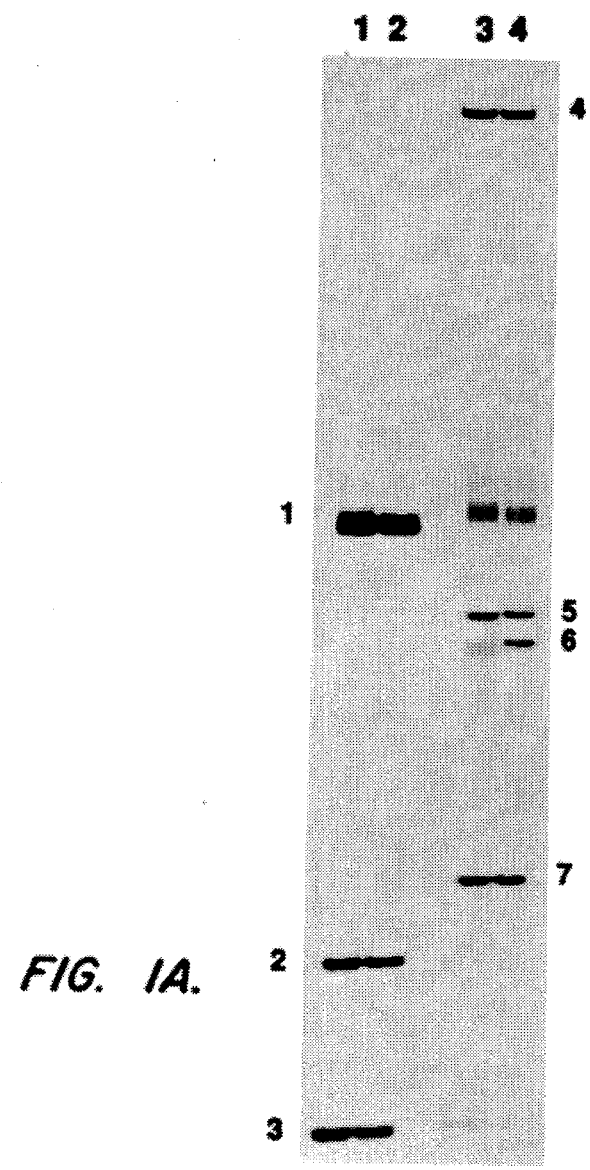
FIG. 1A.
FIG. 1B.
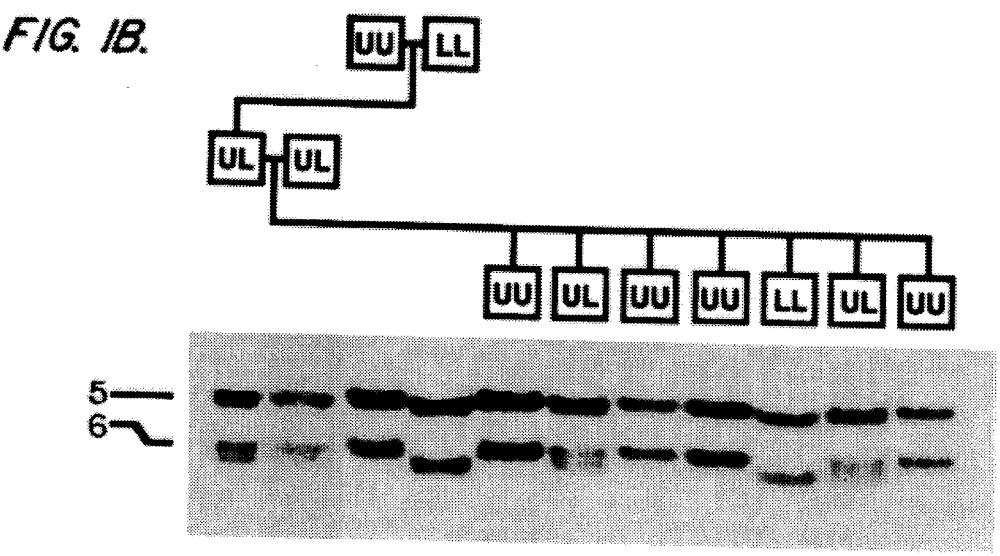

```
LLGEN ASSEMB/PR12END    1 CTTATCACCA AGAGATTCT TATCAGGTTT AGCCTTTCGA GTTTTTCACT  50
JUGEN ASSEMB/PR12END    1 CTTATCACCA AGAGATTCT TATCAGGTTT AGCCTTTCGA GTTTTTCACT  50
                          ---------- --------- ---------- ---------- ----------

LLGEN ASSEMB/PR12END   51 GCACTCAATA TGTGAGACAC AGTTCAGATC CCTTCTATAC CCCAGAGCCG 100
JUGEN ASSEMB/PR12END   51 GCACTCAATA TGTGAGACAC AGTTCAGATC CCTTCTATAC CCCAGAGCCG 100
                          ---------- ---------- ---------- ---------- ----------

LLGEN ASSEMB/PR12END  101 TAAGTACTTC TATTTCAGCC AGGAATTCAT CAAATGGTTA TTTATAATAA 150
JUGEN ASSEMB/PR12END  101 TAAGTACTTC TATTTCAGCC AGGAATTCAT CAAATGGTTA TTTATAATAA 150
                          ---------- ---------- ---------- ---------- ----------

LLGEN ASSEMB/PR12END  151 TGGCATCTAC CTTATGGGTT CTTTTTTTTT TTTTTTTTTT TTGGTGTGCG 200
JUGEN ASSEMB/PR12END  151 TGGCATCTAC CTTATGGGTT CTTTTTTTTT TTTTTTTTTT TTGGTGTGCG 200
                          ---------- ---------- ---------- ---------- ----------

LLGEN ASSEMB/PR12END  201 AGGATTAAAT AAATTAGCAC ATGTGAAGCA TTTAGAATGG TACCTGGCAT 250
JUGEN ASSEMB/PR12END  201 AGGATTAAAT AAATTAGCAC ATGTGAAGCA TTTAGAATGG TACCTGGCAT 250
                          ---------- ---------- ---------- ---------- ----------

LLGEN ASSEMB/PR12END  251 GAAATACATG TTCCATGCTC TATATGTGTT AGCCATTATG ATTATTAATT 300
JUGEN ASSEMB/PR12END  251 GAAATACATG TTCCATGCTC TATATGTGTT AGCCATTATG ATTATTAATT 300
                          ---------- ---------- ---------- ---------- ----------

LLGEN ASSEMB/PR12END  301 GACAACCTAT TAGGTGCTAG CTSCTATTCT GAGCATAGGG AATGTAACAC 350
JUGEN ASSEMB/PR12END  301 GACAACCTAT TAGGTGATAG CTCCTATTCT GAGCATAGGG AATGTAACAC 350
                          ---------- ------*--- ---*------ ---------- ----------
```

FIG. 6-1.

```
LLGEN ASSEMB/PR12END  351 TGAAAAAAAT CAGACACACA TTTCTSCCTG CATAAAGCTT GTATTCCAGT 400
JUGEN ASSEMB/PR12END  351 TGAAAAAAAT CAGACACACA TTTCTCCCTG CATAAAGCTT GTATTCCAGT 400
                                                       *

LLGEN ASSEMB/PR12END  401 GGGGGAAACA GATAATAAMC ACACAAGTAA ATGTTATSCAC ATGTTGCATC 450
JUGEN ASSEMB/PR12END  401 GGGGGAAACA GATAATAAMC ACACAAGTAA ATGTTATSCAC ATGTTGCATC 450

LLGEN ASSEMB/PR12END  451 GAGTGGTGTT GAGTCCCATG GAGAAAAATA AAGCTGAGAA AGGGGGATGG 500
JUGEN ASSEMB/PR12END  451 GAGTGGTGTT GAGTCCCATG GAGAAAAATA AAGCTGAGAA AGGGGGATGG 500

LLGEN ASSEMB/PR12END  501 AGGAAAGTGT AGGTGGGTGG GAGTGTGTGT GTGTGTTGCT GTTTTGAAAA 550
JUGEN ASSEMB/PR12END  501 AGGAAAGTGT AGGTGGGTGG GAGTGTGTGT GTGTGTTGCT GTTTTGAAAA 550

LLGEN ASSEMB/PR12END  551 GGGTGATCAG GGAAGGCCTT GCTGAGAAGG TGATATCTGA GCAGAGATCT 600
JUGEN ASSEMB/PR12END  551 GGGTGATCAG GGAAGGCCTT GCTGAGAAGG TGATATCTGA GCAGAGATCT 600

LLGEN ASSEMB/PR12END  601 GATTTGGGTG TGTATGTGGT GGGGTTGGGT GTTGGGGGTT GTGGTTTTGG 650
JUGEN ASSEMB/PR12END  601 GATTTGGGTG TGTATGTGGT GGGGTTGGGT GTTGGGGGTT GTGGTTTTGG 650

LLGEN ASSEMB/PR12END  651 GAGTGGCATG TGGATGTCCA TAGGTATCTG ATGTGCACTG ATATGTGTGA 700
JUGEN ASSEMB/PR12END  651 GAGTGGCATG TGGATGTCCA TAGGTATCTG ATGTGCACTW ATATGTGTGA 700
```

*FIG. 6-2.*

```
LLGEN ASSEMB/PR12END  701 GTCTGAGTGG CCAAGGTTTT GAACCAAAAT TGTTTCTTTA TTTGATTAGT  750
JUGEN ASSEMB/PR12END  701 GTCTGAGTGG CCAAGGTTTT GAACCAAAAT TGTTTCTTTA TTTGATTAGT  750

LLGEN ASSEMB/PR12END  751 GTCCTTTGTG ATCCATTACT AAAGTATTAT CACCCGATCA TTAGAATAAA  800
JUGEN ASSEMB/PR12END  751 GTCCTTTGTG ATCCATTACT AAAGTATTAT CACCCGATCA TTAGAATAAA  800

LLGEN ASSEMB/PR12END  801 ATATTGGATT TCGATTTGAT TGAATGGTTG ATTATAAACG TATGTTAAGC  850
JUGEN ASSEMB/PR12END  801 ATATTGGATT TCGATTTGAT TGAATGGTTG ATTATAAACG TATGTTAAGC  850

LLGEN ASSEMB/PR12END  851 ACTGCAGCGT GACAAACTTG TACCTCTCTT TCAGAGATAC CTGCCATGAA  900
JUGEN ASSEMB/PR12END  851 ACTGCAGCGT GACAAACTTG TACCTCTATT* TCAGAGATAC CTGCCATGAA  900

LLGEN ASSEMB/PR12END  901 CTCTTAGGTC ATGTCCCGCT TTTGGCTGAA CCTAGTTTTG CCCAATTCTC  950
JUGEN ASSEMB/PR12END  901 CTCTTAGGTC ATCTCCCGCT TTTGGCTGAA CCTAGTTTTG CCCAATTCTC  950

LLGEN ASSEMB/PR12END  951 CCAAGAAATT GGCTTGGCTT CTCTTG  976
JUGEN ASSEMB/PR12END  951 CCAAGAAATT GGCTTGGCTT CTCTTG  976
```

*FIG. 6-3.*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( v i ) ORIGINAL SOURCE:
      ( A ) ORGANISM: Homo sapiens ( x i ) SEQUENCE DESCRIPTION: SEQ ID NO:1:

GCGGACTTGG CTATGAACTA TAAAC 25

( 2 ) INFORMATION FOR SEQ ID NO:2:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( v i ) ORIGINAL SOURCE:
      ( A ) ORGANISM: Homo sapiens ( x i ) SEQUENCE DESCRIPTION: SEQ ID NO:2:

AATCTCCTCT TCAGTGAATT CAACC 25

( 2 ) INFORMATION FOR SEQ ID NO:3:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( v i ) ORIGINAL SOURCE:
      ( A ) ORGANISM: Homo sapiens ( x i ) SEQUENCE DESCRIPTION: SEQ ID NO:3:

TTCAGATCCC TTCTATACCC CAGAG 25

( 2 ) INFORMATION FOR SEQ ID NO:4:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear (ii) MOLECULE TYPE: DNA (genomic)

(iii) HYPOTHETICAL: NO (vi) ORIGINAL SOURCE:
  (A) ORGANISM: Homo sapiens (xi) SEQUENCE DESCRIPTION: SEQ ID NO:4:

GGACATGACC TAAGAGTTCA TGGCA                    25

(2) INFORMATION FOR SEQ ID NO:5:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (iii) HYPOTHETICAL: NO (vi) ORIGINAL SOURCE:
    (A) ORGANISM: Homo sapien (xi) SEQUENCE DESCRIPTION: SEQ ID NO:5:

CCTCTCTTTC                                      10

(2) INFORMATION FOR SEQ ID NO:6:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (iii) HYPOTHETICAL: NO (vi) ORIGINAL SOURCE:
    (A) ORGANISM: Homo sapien (xi) SEQUENCE DESCRIPTION: SEQ ID NO:6:

TGCTAGCTSC TATTCT                               16

(2) INFORMATION FOR SEQ ID NO:7:

(i) SEQUENCE CHARACTERISTICS:
    (A) LENGTH: 976 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: Homo sapien (ix) FEATURE:
    (A) NAME/KEY: misc_feature
    (B) LOCATION: 1..973
    (D) OTHER INFORMATION: /standard_name= "The U allele DNA
      sequence from the human TPH gene"
      / note= "The U allele DNA sequence for the region
      of the human TPH gene surrounding and including
      the intron corresponding to intron 7 of the mouse (xi) SEQUENCE DESCRIPTION: SEQ ID NO:7:

CTTATCACCA AGAGATTTCT TATCAGGTTT AGCCTTTCGA GTTTTTCACT GCACTCAATA    60

TGTGAGACAC AGTTCAGATC CCTTCTATAC CCCAGAGCCG TAAGTACTTC TATTTCAGCC   120

AGGAATTCAT CAAATGGTTA TTTATAATAA TGGCATCTAC CTTATGGGTT CTTTTTTTTT   180

TTTTTTTTTT TTGGTGTGCG AGGATTAAAT AAATTAGCAC ATGTGAAGCA TTTAGAATGG   240

| | | | | | | |
|---|---|---|---|---|---|---|
| TACCTGGCAT | GAAATACATG | TTCCATGCTC | TATATGTGTT | AGCCATTATG | ATTATTAATT | 300 |
| GACAACCTAT | TAGGTGATAG | CTCCTATTCT | GAGCATAGGG | AATGTAACAC | TGAAAAAAAT | 360 |
| CAGACACACA | TTTCTCCCTG | CATAAAGCTT | GTATTCCAGT | GGGGGAAACA | GATAATAAMC | 420 |
| ACACAAGTAA | ATGTATSCAC | ATGTTGCATC | GAGTGGTGTT | GAGTCCCATG | GAGAAAATA | 480 |
| AAGCTGAGAA | AGGGGGATGG | AGGAAAGTGT | AGGTGGGTGG | GAGTGTGTGT | GTGTGTTGCT | 540 |
| GTTTTGAAAA | GGGTGATCAG | GGAAGGCCTT | GCTGAGAAGG | TGATATCTGA | GCAGAGATCT | 600 |
| GATTTGGGTG | TGTATGTGGT | GGGGTTGGGT | GTTGGGGGTT | GTGGTTTTGG | GAGTGGCATG | 660 |
| TGGATGTCCA | TAGGTATCTG | ATGTGCACTW | ATATGTGTGA | GTCTGAGTGG | CCAAGGTTTT | 720 |
| GAACCAAAAT | TGTTTCTTTA | TTTGATTAGT | GTCCTTTGTG | ATCCATTACT | AAAGTATTAT | 780 |
| CACCCGATCA | TTAGAATAAA | ATATTGGATT | TCGATTTGAT | TGAATGGTTG | ATTATAAACG | 840 |
| TATGTTAAGC | ACTGCAGCGT | GACAAACTTG | TACCTCTATT | TCAGAGATAC | CTGCCATGAA | 900 |
| CTCTTAGGTC | ATGTCCCGCT | TTTGGCTGAA | CCTAGTTTTG | CCCAATTCTC | CCAAGAAATT | 960 |
| GGCTTGGCTT | CTCTTG | | | | | 976 |

( 2 ) INFORMATION FOR SEQ ID NO:8:

( i ) SEQUENCE CHARACTERISTICS:
        ( A ) LENGTH: 976 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapien ( i x ) FEATURE:
        ( A ) NAME/KEY: misc_feature
        ( B ) LOCATION: 1..971
        ( D ) OTHER INFORMATION: /standard_name= "The L allele DNA
            sequence from the human TPH gene"
            / note= "The L allele DNA sequence for the region
            of the human TPH gene surrounding and including
            the intron corresponding to intron 7 of the mouse ( x i ) SEQUENCE DESCRIPTION: SEQ ID NO:8:

| | | | | | | |
|---|---|---|---|---|---|---|
| CTTATCACCA | AGAGATTTCT | TATCAGGTTT | AGCCTTTCGA | GTTTTCACT | GCACTCAATA | 60 |
| TGTGAGACAC | AGTTCAGATC | CCTTCTATAC | CCCAGAGCCG | TAAGTACTTC | TATTTCAGCC | 120 |
| AGGAATTCAT | CAAATGGTTA | TTTATAATAA | TGGCATCTAC | CTTATGGGTT | CTTTTTTTTT | 180 |
| TTTTTTTTTT | TTGGTGTGCG | AGGATTAAAT | AAATTAGCAC | ATGTGAAGCA | TTTAGAATGG | 240 |
| TACCTGGCAT | GAAATACATG | TTCCATGCTC | TATATGTGTT | AGCCATTATG | ATTATTAATT | 300 |
| GACAACCTAT | TAGGTGCTAG | CTSCTATTCT | GAGCATAGGG | AATGTAACAC | TGAAAAAAAT | 360 |
| CAGACACACA | TTTCTSCCTG | CATAAAGCTT | GTATTCCAGT | GGGGAAACA | GATAATAAMC | 420 |
| ACACAAGTAA | ATGTATSCAC | ATGTTGCATC | GAGTGGTGTT | GAGTCCCATG | GAGAAAATA | 480 |
| AAGCTGAGAA | AGGGGGATGG | AGGAAAGTGT | AGGTGGGTGG | GAGTGTGTGT | GTGTGTTGCT | 540 |
| GTTTTGAAAA | GGGTGATCAG | GGAAGGCCTT | GCTGAGAAGG | TGATATCTGA | GCAGAGATCT | 600 |
| GATTTGGGTG | TGTATGTGGT | GGGGTTGGGT | GTTGGGGGTT | GTGGTTTTGG | GAGTGGCATG | 660 |
| TGGATGTCCA | TAGGTATCTG | ATGTGCACTW | ATATGTGTGA | GTCTGAGTGG | CCAAGGTTTT | 720 |
| GAACCAAAAT | TGTTTCTTTA | TTTGATTAGT | GTCCTTTGTG | ATCCATTACT | AAAGTATTAT | 780 |
| CACCCGATCA | TTAGAATAAA | ATATTGGATT | TCGATTTGAT | TGAATGGTTG | ATTATAAACG | 840 |

```
TATGTTAAGC ACTGCAGCGT GACAAACTTG TACCTCTCTT TCAGAGATAC CTGCCATGAA    900

CTCTTAGGTC ATGTCCCGCT TTTGGCTGAA CCTAGTTTTG CCCAATTCTC CCAAGAAATT    960

GGCTTGGCTT CTCTTG                                                    976
```

METHOD FOR DETECTING ABNORMAL SEROTONERGIC FUNCTION

This application is a continuation-in-part of U.S. patent application Ser. No. 07/873,913 filed on Apr. 24, 1992, now abandoned which is incorporated herein by reference and benefit is claimed of its filing date.

BACKGROUND OF THE INVENTION

The present invention relates to novel methods for predicting suicidal and other abnormal behaviors. In particular, it relates to the detection of polymorphisms in the tryptophan hydroxylase gene, which are correlated with abnormal serotonergic function and related behaviors.

Genetic factors have been implicated in the etiology of alcoholism, violence, and suicide in both family and twin studies. A strong interrelationship exists between these phenotypes, as they tend to occur in the same individual and in individuals who are genetically closely related. Although these disorders are heterogeneous in their clinical expression, and have complex causes, it is possible to identify more homogeneous subgroups among patients with these problems.

Decreased brain serotonin concentration has been associated with several behavioral traits including impulsive, aggressive and suicidal behavior, pyromania (fire setting), and with disruption of circadian rhythms. For a review of the correlation between serotonin concentrations and abnormal behavior see, Lopez-Ibor et al. (1991) In *Serotonin-related psychiatric syndromes: clinical and therapeutic links* (Ed. Cassano and Akiskal, Royal Society of Medicine Services Ltd.) pp. 35–40. Serotonergic activity is correlated with the concentration of the serotonin metabolite 5-hydroxyindoleacetic acid (5-HIAA) in the cerebrospinal fluid (Asberg et el. (1976) *Arch. Gen. Psychiatry* 33: 1193–1197).

Low concentrations of 5-HIAA in the cerebrospinal fluid (CSF) have been associated with behaviors characterized by intolerance to delay, or impulsive behavior. These include impulsive aggression (including homicide), pyromania (fire setting), personality disorders, and alcoholism. Serotonin is also critical in slow-wave sleep, temperature control, and appetitive behaviors. Diminished CSF 5-HIAA concentrations have been found to be associated with risk of suicide in depressed patients. In animal studies, indices of decreased serotonin concentrations are connected with postulated anxiety-related intolerance to delay and deficient control of impulses.

Although 5-HIAA concentrations in CSF are correlated with abnormal serotonergic behaviors, 5-HIAA's usefulness as a marker is limited by the difficulty in obtaining CSF. CSF may only be obtained by an invasive, expensive, and impractical procedure. Thus, there is a need for an easily typed marker that is correlated with 5-HIAA levels and abnormal serotonergic behaviors. The present invention fulfills this and other needs.

SUMMARY OF THE INVENTION

The invention provides a method of predicting abnormal serotonergic function in an impulsive human subject, the method comprising detecting an L allele of a gene encoding tryptophan hydroxylase. In a preferred embodiment, the L allele is in a homozygous state. The L allele may be detected in nucleic acids isolated from the subject by polymerase chain reaction, and other methods. The L allele may also be detected by single strand conformation polymorphism analysis. In one embodiment, the L allele is associated with a polymorphism within an intron of the gene encoding tryptophan hydroxylase; preferably, the intron corresponds to intron 7 of a mouse gene encoding tryptophan hydroxylase. The abnormal serotonergic function may be a behavior, in particular, suicidal behavior or pyromania. Also claimed are an isolated nucleic acid comprising a sequence specific to a subsequence of an L allele of a gene encoding tryptophan hydroxylase. The nucleic acid may be obtained by polymerase chain reaction amplification. The nucleic acid may migrate in a denaturing gel at the same rate as a second nucleic acid specific to a corresponding region of a U allele of a gene encoding tryptophan hydroxylase; and migrate in a nondenaturing gel at a rate about 1.02 times the migration rate of the second nucleic acid. The nucleic acid sequence may be specific to a subsequence of the L allele comprising an intron, preferably the intron corresponds to intron 7 of a mouse gene encoding tryptophan hydroxylase.

DEFINITIONS

An "impulsive human subject" refers to a person deficient in normal behavioral balances and controls. Such behavior includes disorders categorized in the Diagnostic and Statistical Manual of Mental Disorders (*Diagnostic and Statistical Manual of Mental Disorders, Third Edition-Revised* (DSM-III-R), Spitzer, R. L., Chair, Workshop to revise DSM-III, Press syndicate of the Univ. of Cambridge, Cambridge, UK, 1987, which is incorporated herein by reference). The diagnosis of impulsivity using DSM-III is described by, e.g., Woodcock (1986) *Psychiatric Clinics of North America*, 9: 341–352. Certain non-premeditated crimes (e.g., homicide, arson and assault) committed by a subject may also be indicative of impulsivity.

"Abnormal serotonergic function" refers to disorders that are correlated with a deviation from the norm in serotonergic activity caused by changes in serotonin synthesis, metabolism, or utilization. Typically, abnormal serotonergic activity is detected by measuring 5-HIAA levels. Such disorders include, but are not limited to, suicidal behavior and pyromania.

"Polymorphism" refers to a nucleotide or nucleotides that are different (typically as the result of nucleotide substitutions, deletions, or insertions) when homologous regions of DNA are compared among two or more individuals.

"Homologous" refers to nucleotide sequences within the genomes of two or more individual organisms (of the same or different species) that carry out the same function in each of the individuals, such as coding for a particular protein or portion of a protein. The nucleotide sequences of the homologous regions may be the same or different when compared among the different individuals. For example, the human gene that codes for tryptophan hydroxylase is said to be homologous to the mouse tryptophan hydroxylase gene.

An "allele" is one of several alternate forms of a gene, which occupies a particular locus on a chromosome.

A polymorphism is said to be "homozygous" or in a "homozygous state" if the same allele for a particular locus, as identified by available methods, is present on each of the two homologous chromosomes in a diploid cell from an individual organism.

A polymorphism is said to be "linked to" a gene if the recombination frequency between the polymorphism and the gene is less than about 0.5, preferably less than about 0.25. The polymorphism may be either within or outside the gene.

A polymorphism is said to be "associated with" an allele of a gene if the frequency of the polymorphism is higher in individuals having the allele than in people without the allele. The polymorphism may be either within or outside the gene.

A sequence in a gene is said to "correspond to" a sequence in the homologous gene from another organism if the sequence occurs between or within approximately the same flanking sequences or codons as the corresponding sequence in the other organism. For example, an intron in the human TPH gene that lies between the codon for amino acid 42 and the codon for amino acid 43 in the mouse TPH gene is said to correspond to intron 2 of the mouse TPH gene.

"Amplifying" or "amplification" which typically refers to an "exponential" increase in target nucleic acid, is used herein to describe both linear and exponential increases in the numbers of a select target sequence of nucleic acid. Amplification can be carried out according to a number of methods well known to those of skill in the art. Examples of such methods include polymerase chain reaction (PCR), ligase chain reaction (LCR), RNA transcription-based amplification systems, and the like.

"Bind(s) substantially" refers to complementary hybridization between an oligonucleotide and a target sequence and embraces minor mismatches which can be accommodated by reducing the stringency of the hybridization media to achieve the desired priming for the PCR polymerases or detection of hybridization signal.

"Isolated" refers to material that is substantially or essentially free from components which normally accompany it as found in its native state. For instance, affinity purified antibodies or monoclonal antibodies exits in a biologically purified state.

"Hybridizing" refers the binding of two single stranded nucleic acids via complementary base pairing.

"Nucleic acid" refers to a deoxyribonucleotide or ribonucleotide polymer in either single- or double-stranded form, and unless otherwise limited, would encompass known analogs of natural nucleotides which can function in a similar manner as naturally occurring nucleotides.

"Primer" or "nucleic acid polymerase primer(s)" refers to an oligonucleotide, whether natural or synthetic, capable of acting as a point of initiation of DNA synthesis under conditions in which synthesis of a primer extension product complementary to a nucleic acid strand is initiated, i.e., in the presence of four different nucleotide triphosphates and an agent for polymerization (i.e., DNA polymerase or reverse transcriptase) in an appropriate buffer and at a suitable temperature. A primer is preferably an oligodeoxyribonucleotide and is single stranded for maximum efficiency in amplification, but may also be double stranded. If double stranded, the primer is first treated to separate its strands before being used to prepare extension products. The exact length of a primer will depend on many factors, but typically ranges from 15 to 25 nucleotides. Short primer molecules generally require cooler temperatures to form sufficiently stable hybrid complexes with the template. A primer need not reflect the exact sequence of the template, but must be sufficiently complementary to hybridize with a template. An example of a non-complementary sequence which may be incorporated into the primer is a sequence which encodes a restriction enzyme recognition site (see U.S. Pat. No. 4,800,159).

A primer can be labeled, if desired, by incorporating a label detectable by spectroscopic, photochemical, biochemical, immunochemical, or chemical means. For example, useful labels include $^{32}p$, fluorescent dyes, electron-dense reagents, enzymes (as commonly used in ELISAs), biotin, or haptens or proteins for which antisera or monoclonal antibodies are available. A label can also be used to "capture" the primer so as to facilitate the immobilization of either the primer or amplified DNA on a solid support.

"Probe" refers to an oligonucleotide which binds through complementary base pairing to a subsequence of a target nucleic acid. It will be understood by one of skill in the art that probes will typically substantially bind target sequences lacking complete complementarity with the probe sequence depending upon the stringency of the hybridization conditions. The probes are preferably directly labelled as with isotopes or indirectly labelled such as with biotin to which a streptavidin complex may later bind. By assaying for the presence or absence of the probe, one can detect the presence or absence of the target.

"Recombinant" when referring to a nucleic acid probe refers to an oligonucleotide which is free of native proteins and nucleic acid typically associated with probes isolated from the cell which naturally contains the probe sequence as a part of its native genome. Recombinant probes include those made by amplification means such as PCR and genetic cloning methods where bacteria are transformed with the recombinant probe.

A "sequence specific to" a particular allele is a sequence unique to the allele, that is, not shared by other characterized alleles of the gene. A probe containing a subsequence complementary to a sequence specific to an allele will typically not hybridize to the corresponding portion of the genome of other isolates under stringent conditions (e.g., washing the solid support in 2x SSC, 0.1% SDS at 70° C.).

The term "substantially identical" indicates that two or more nucleotide sequences share a majority of their sequence. Generally, this will be at least about 90% of their sequence and preferably about 95% of their sequence. Another indication that sequences are substantially identical is if they hybridize under stringent conditions (see, e.g., Sambrook et al., *Molecular Cloning—A Laboratory Manual,* Cold Spring Harbor Laboratory, Cold Spring Harbor, N.Y., 1985. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.2 molar at pH 7 and the temperature is at least about 60° C.

"Subsequence" refers to a sequence of nucleic acids which comprise a part of a longer sequence of nucleic acids.

"Target region" or "region" refers to a subsequence of a nucleic acid which is to be analyzed, which usually contains polymorphic DNA sequences.

BRIEF DESCRIPTION OF THE FIGURES

FIGS. 1A and 1B present SSCP analysis of the human TPH "intron 7". FIG. 1A is an autoradiogram of nondenatured DNA samples, lanes 1 and 2 versus denatured DNA samples (SSCP), lane 3 and 4, electrophoresed on a nondenaturing gel. The bands corresponding to the U and L alleles are indicated. FIG. 1B shows transmission of the TPH polymorphism in a CEPH family, as analyzed by SSCP. The pedigree displayed at the top corresponds to the lanes below.

FIG. 6 shows the U (Seq. ID No.:7) and L (Seq. ID No.:8) allele DNA sequences for the region of the human TPH gene surrounding and including the intron corresponding to intron number 7 of the mouse TPH gene.

DESCRIPTION OF THE PREFERRED EMBODIMENTS

Figure 2:
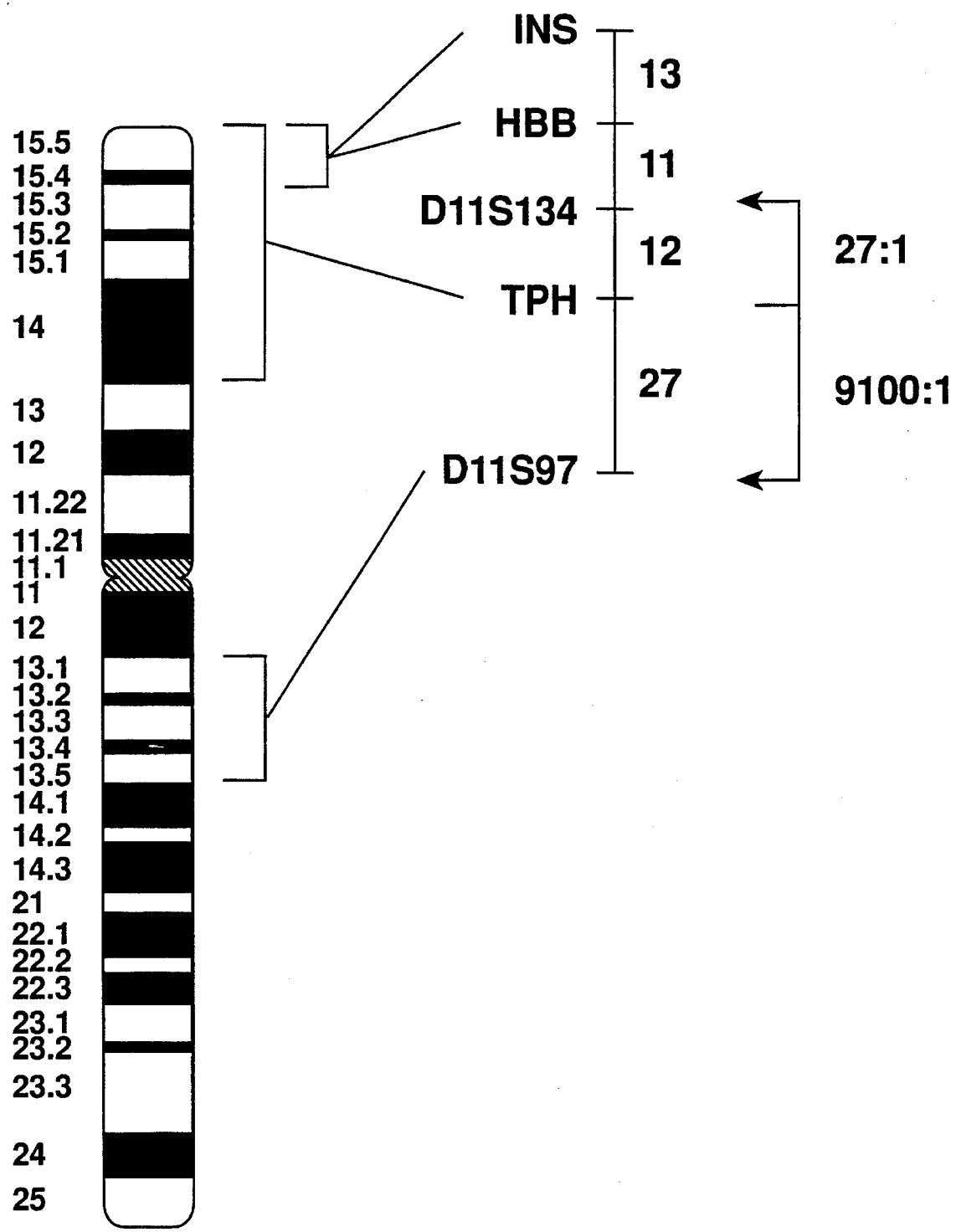
FIG. 2 presents information on the genetic location of the human TPH gene in relation to other mapped chromosome 11 loci. Odds against the placement of TPH in adjacent positions are shown.

This invention discloses methods for detecting polymorphisms associated with certain alleles of the tryptophan hydroxylase (TPH) gene that are useful in predicting abnormal serotonergic behaviors in impulsive subjects. Tryptophan hydroxylase (TPH) (EC 1.14.16.4) catalyzes the biopterin-dependent, monooxygenation of tryptophan to 5-hydroxytryptophan (Jequier et al. (1969) *Biochem. Pharmacol.* 18: 1071–1081; Kaufman (1987) in *Amino acids in health and disease: new perspectives,* Alan R. Liss, Inc., pp. 205–232) which is subsequently decarboxylated to form the neurotransmitter serotonin. Monoamine oxidase A, and to a lesser extent monoamine oxidase B, then deaminates serotonin, which subsequently is oxidized to form 5-hydroxyindoleacetic acid (5-HIAA). TPH expression is limited to a few specialized tissues in humans, including raphe neurons, pinealocytes, mast cells, mononuclear leucocytes and intestinal mucosa cells. In the raphe neurons of the brainstem, TPH is the rate-limiting enzyme in the biosynthesis of serotonin (Cooper et al., (1961) *J. Pharmacol Exp. Therap.* 132:265–268.

TPH is the rate-limiting enzyme in the biosynthesis of serotonin. Grahame-Smith (1964) *Biochem. Biophys. Res. Commun.* 16: 586. Thus, polymorphic alleles that mark functional variants of a TPH gene can be correlated with CSF 5-HIAA concentration and with abnormal serotonergic function and related behaviors in impulsive subjects.

The TPH gene has been cloned from mouse (Stoll and Goldman (1991) *J. Neurosci. Res.* 28: 457–465) and TPH cDNAs have been isolated from human (Boularand et al. (1990) *Nucl. Acids Res.* 18: 4257), mouse (Stoll et al. (1990) *Genomics* 7: 88–96), rat (Kim et al. (1991) *Mol. Brain Res.* 9: 277–283), and rabbit (Grenett et al. (1987) *Proc. Natl. Acad. Sci.* USA 84: 5530–5534). These homologous TPH genes have a high degree of sequence identity. Using somatic cell hybrids, the human TPH gene has been localized to the short arm of chromosome 11 (Ledley et al. (1987) *Somatic Cell Mol. Genetics* 13: 575–580) and, by in situ hybridization, to the chromosome region 11p15.3→p14 (Craig (1991) *Cytogenet. Cell Genet.* 42: 29–32).

A linkage of bipolar affective disorder to chromosomal region 11p15 has been observed (Egeland et al. (1987) *Nature* 325: 783–787). Subsequent studies, however, have greatly weakened this result (reviewed in Ciaranello and Ciaranello (1991) *Ann. Rev. Med.* 42: 151–158). A recent study (Pakstis (1991) *Human Genet.* 87: 475–483) revealed that LOD (log of the odds) scores at this region remain slightly positive. A low but positive LOD score may indicate genetic heterozygosity, partial penetrance or the inclusion of nongenetic cases.

Evidence provided here indicates that polymorphisms in the TPH gene are valuable tools for studying the genetic linkage of TPH to various serotonergic behaviors in impulsive subjects. The two TPH alleles (U and L) occur with the same frequency in the impulsive and non-impulsive groups. In impulsive groups, however, there is a significant correlation of abnormal serotonergic function, and related behaviors, with TPH genotype.

These polymorphisms usually have an effect on TPH activity and thus also affect serotonin biosynthesis. Alternatively, the polymorphisms may be linked to a separate mutation at the TPH locus that would alter the activity, expression or regulation of the TPH gene. Based on the detection of these polymorphisms, the present invention provides methods for determining whether a subject is likely to attempt suicide or homicide, set fires, or exhibit other abnormal behaviors.

In the exemplified methods described below, abnormal serotonergic function, and related behaviors, in impulsive subjects are correlated with the presence of a polymorphism that is associated with the L allele of the tryptophan hydroxylase gene. The presence of the L allele in the homozygous state, meaning that the L allele is carried on both of the homologous chromosomes that carry the tryptophan hydroxylase gene (chromosome 11), is an even stronger predictor of abnormal serotonergic function than a heterozygous polymorphism. The particular polymorphic site detected in the example is located within an intron of the human TPH gene that corresponds to intron 7 of the mouse TPH gene (Stoll et al. (1991) *J. Neuroscience Res.* 28: 457–465, which is incorporated herein by reference).

The polymorphisms or alleles associated with the polymorphisms can be detected and used in a number of different ways. For instance, if a TPH functional variant were transmitted in a family, the identification of a marker polymorphism associated with the gene would enable one to predict with great confidence whether the TPH functional variant was transmitted from parent to offspring. Alternatively, one can analyze nucleic acids isolated from the individual using standard techniques. For instance, one can use nucleic acid primers or probes for amplifying or detecting the polymorphisms or nucleic acids that are closely linked to these polymorphisms.

Several techniques are available for detecting nucleic acid sequences comprising, or associated with, the polymorphisms. These methods include, but are not limited to, polymerase chain reaction-single strand conformational polymorphism (PCR-SSCP), ligase chain reaction (Barany (1991) *Proc. Natl. Acad. Sci.* USA 88: 189–193; Wu et al. (1989) *Genomics* 4: 560–569; Barringer et al. (1990) *Gene* 89: 117–122), restriction fragment length polymorphism (RFLP) (Botstein et al. (1980) *Am. J. Hum. Genet.* 69: 201–205), short tandem repeats (STR, Dean et al. (1991) *Am. J. Hum. Genet.* 49: 621–626), denaturing gradient gel electrophoresis (Myers et al. (1985) *Nature* 313: 495–498), and oligonucleotide hybridization (Conner et al. (1983) *Proc. Natl. Acad. Sci.* USA 83: 5194–5198) (all references incorporated herein by reference).

Single-strand conformational polymorphism (SSCP) analysis is a highly sensitive method for detecting nucleotide sequence variants (Orita et al. (1989) *Proc. Natl. Acad. Sci.* USA 86: 2766–2770; Orita et al. (1989) *Genomics* 5: 874–879, which are incorporated herein by reference). Sequence changes, including single-base substitutions, are detected as shifts in electrophoretic mobility.

Typically, the DNA to be analyzed is obtained by PCR amplification. Labelled primers may be used in the amplification reaction to facilitate detection. The PCR process is well known in the art (see U.S. Pat. Nos. 4,683,195; 4,683, 202; and 4,965,188, each of which is incorporated herein by reference). In addition, commercial vendors sell PCR reagents and publish PCR protocols. Thus, detailed description of PCR protocols is not included here.

The amplified fragment is then analyzed by SSCP, which involves electrophoresis of the fragment in a nondenaturing gel. If the fragment is significantly larger than 200 bp in length, it may be desirable to cleave the fragment with one or more restriction enzymes to obtain the polymorphism on a smaller fragment and thus increase the resolution of the separation. Polymorphic differences between fragments from different DNA sources may be visualized as differences in electrophoretic mobility.

Amplification and SSCP analysis of DNA is demonstrated here to be a highly efficient means of generating polymorphic markers at candidate genes. In addition, it has been found that relatively large sequences can be amplified and cut with restriction enzymes to provide fragments of shorter length which are highly suitable for SSCP analysis. Using this technique, a polymorphism can be discovered by analyzing only a few regions of the gene or sequence of interest. If introns are targeted for analysis, the intron locations and sequences, are not required in advance of this technique, so that cDNA sequence data can be used directly without the necessity of isolating genomic clones.

The polymorphisms of the invention may also be detected by restriction fragment length polymorphism (RFLP) analysis. RFLP analysis is well known to those of skill in the art and is described, for instance in WO 92/00386, which is incorporated herein by reference. Briefly, this technique involves using as probes marker sequences that are located close to the gene or allele of interest. Fragments of a marker gene may be isolated and used directly. Alternatively, if the sequence is known, an oligonucleotide probe may be synthesized based on this sequence. The marker sequence occurs polymorphically, that is, slightly different forms of the marker sequence occur in the population. A particular form of the marker sequence is said to be consistently associated with a particular form, such as a particular allele, of the gene of interest, if the marker sequence is closely linked to the gene of interest so that recombination between the gene of interest and the marker sequence is very rare. A marker sequence is most useful for detecting an abnormality when it is consistently associated with the particular form of the gene of interest that is associated with the abnormality.

Variants of the marker sequence are identified by the different restriction fragment patterns that occur when isolated DNA is digested by one or more restriction enzymes. Polymorphisms located within or near the marker sequence may create or destroy restriction sites. Digesting the DNA with an enzyme for which a site has been created or destroyed may thus result in a different restriction fragment pattern for each polymorphic form. The restriction fragment patterns are most commonly visualized by hybridizing to the digested, electrophoretically fractionated DNA an isolated fragment of the marker sequence that has been detectably labelled.

The invention also includes isolated nucleic acids that are specific to an allele of the TPH gene that is associated with abnormal serotonergic behavior. Typically, the nucleic acids are specific to a subsequence of an intron of a TPH gene. An isolated nucleic acid that includes the intron in the human TPH gene that corresponds to intron 7 of the mouse TPH gene (Stoll et al. (1991) supra) is particularly useful. The isolated nucleic acid may be obtained by polymerase chain reaction amplification, ligase chain reaction, or other amplification methods known to one of skill in the art.

The isolated nucleic acids specific to the desired allele can be detected using the PCR-SSCP techniques discussed above, or can be identified using probes specific to the sequence. The sequence can also be detected using standard hybridization techniques (e.g. Southern hybridizations or dot blots), with or without prior amplification.

The nucleotide sequences of the polymorphisms associated with the U and L alleles may be determined. Determining such sequences is useful for facilitating the use of simpler methods, such as ligase chain reaction, for testing an individual for the presence of each allele. A variety of techniques may be used to determine the U and L allele DNA sequences for both exon and intron regions of the TPH gene. In general, DNA from an individual may be amplified by, e.g. polymerase chain reaction. A variety of probes may be synthesized from the known cDNA sequence of the human TPH gene (See Bouland, S., et al., supra.) for use in PCR protocols. Using appropriate PCR probes, various regions of the gene can be PCR amplified from DNA from individuals known to have or suspected of having the U or L alleles, respectively. The amplified DNA fragment may then be digested with one or more restriction endonuclease enzymes, if necessary, to release the subfragment in which the polymorphism is located. The digested fragment may then be electrophoresed through a nondenaturing gel and the polymorphism-containing fragment can be identified. This fragment can purified from the gel and is cloned into a cloning vector using standard techniques. Alternatively it may be sequenced directly. Cloning and sequencing methods are described in, e.g. Sambrook et al., supra.

The nucleic acid sequence of the human TPH gene intron corresponding to intron 7 of the mouse was determined for both the U and L alleles by using PCR techniques, as described in Example III herein. This region of the sequence of the human TPH gene contains a sequence difference between the U and L allelles, as determined by SSCP analysis (See Example 1, herein.) The sequence of the L and U alleles for this region of the human TPH gene is shown in FIG. 6, herein.

The differences in DNA sequence between the L and U alleles may be used to design nucleic acid probes capable of distinguishing the U and L alleles in diagnostic tests. For example, the one base G-C to A-T mutations at positions 317 and 878 in FIG. 1 may be detected by selecting and synthesizing probes capable of selectively hybridizing to the DNA sequence of either the U or L allele. The length of the probe and the hybridization conditions used to detect the L allele mutation depends on the surrounding sequence, and may be determined experimentally. (See Sambrook, et al., supra.)

A variety of methods of specific DNA measurement using nucleic acid hybridization techniques are known to those of skill in the art. See Sambrook, et al., supra. For example, one method for evaluating the presence or absence of the L gene allele in a sample involves a Southern transfer. Briefly, the digested genomic DNA is run on agarose slab gels in buffer and transferred to membranes. Hybridization is carried out using the probes discussed above. Visualization of the hybridized portions allows the determination of the presence or absence of the L allele.

A variety of nucleic acid hybridization formats are known to those skilled in the art. For example, common formats include sandwich assays and competition or displacement assays. Hybridization techniques are generally described in "Nucleic Acid Hybridization, A Practical Approach," Ed. Hames, B. D. and Higgins, S. J., IRL Press, 1985; Gall and Pardue (1969), *Proc. Natl. Acad. Sci.*, U.S.A., 63:378–383; and John, Burnsteil and Jones (1969) *Nature*, 223:582–587, all incorporated herein by reference.

The sensitivity of the hybridization assays may be enhanced through use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA), Cangene, Mississauga, Ontario) and Q Beta Replicase systems.

This invention also embraces diagnostic kits for detecting the presence of the L allele in blood or tissue samples which comprise a container containing an oligonucleotide probe or probes specific for the L or U allele and instructional material for performing the test.

Nucleic acid sequences (e.g., genomic DNA, cDNA, or RNA) from the TPH alleles of the invention can be also used in a variety of recombinant expression systems to obtain expression of the encoded proteins. Recombinant expression of nucleotide sequences in prokaryotic or eukaryotic hosts is well known in the art. See Sambrook et al., *Molecular Cloning–A Laboratory Manual*, Cold Spring Harbor Laboratory, Cold Spring Harbor, N.Y., 1985. The expressed proteins can be used to raise immunoglobulins specific to the alleles associated with abnormal serotonergic.

The immunoglobulins, e.g., monoclonal antibodies, may be used for a variety of applications. For instance they can be used to assay for the presence of the TPH enzyme encoded by a particular allele in a biological sample. For a discussion of general procedures of monoclonal antibody production see Harlow and Lane, *Antibodies, A Laboratory Manual*, Cold Spring Harbor Publications, N.Y. (1988), which is incorporated herein by reference. The immunoglobulins can be detected using standard labelling systems well known to those of skill in the art.

EXAMPLE I

This example demonstrates the genetic mapping of the human tryptophan hydroxylase gene to chromosome 11 p15.5 using an intronic conformational polymorphism. By examining introns of the human TPH gene by PCR amplification and analysis by the single-strand conformational polymorphism (SSCP) technique, an SSCP was revealed with two alleles that occur with frequencies of 0.40 and 0.60 in unrelated Caucasians.

DNAs from 24 informative Centre d'Etude Polymorphisme Humain (CEPH) families (Dausset et al. (1990) *Genomics* 6575–577) were typed for the TPH intron polymorphism and analyzed with respect to eight linked markers on chromosome 11 between p13 and p15 with the result that TPH was placed near HBB at chromosomal region 15.5. This region contains loci for several important genes including those for Wiedemann-Beckwith Syndrome and tyrosine hydroxylase.

Materials and Methods
a) Polymerase chain reaction, single-strand conformational polymorphism analysis.

Polymerase chain reactions were performed on two regions of human TPH gene. In the following discussions, intron and exon numbers are those which correspond to the intron and exon locations in the mouse TPH gene. The first region extends from the 3' end of exon 5, through the intron that corresponds to intron 5 of the mouse TPH gene, and to the 5' end of exon 6. The second region extends from the 3' end of exon 7, through intron 7, and to the 5' end of exon 8. The "intron 5" region was amplified with the primers HTHSSCP1 and HTHSSCP3 that correspond to the human TPH sequence and amplify a region of approximately 230 base pairs. The "intron 7" region was amplified with the primers HTHSSCP4 and HTHSSCP5 that correspond to the human TPH sequence and amplify a region of approximately 890 base pairs. The primer sequences are:

HTHSSCP1: 5'-GCGGACTTGGCTATGAAC-TATAAAC-3' (Seq. ID No.:1)
HTHSSCP3: 5'-AATCTCCTCTTCAGTGAAT-TCAACC-3' (Seq. ID No.:2)
HTHSSCP4: 5'-TTCAGATCCCTTCTATACCCCA-GAG-3' (Seq. ID No.:3)
HTHSSCP5: 5'-GGACATGACCTAAGAGTTCATG-GCA-3' (Seq. ID No.:4)

Amplification was performed using 100 ng of human DNA, 0.2 µM of each primer, 250 µM each of dCTP, dGTP, dTTP and dATP, 250 µM spermidine, 50 mM KCl, 1.5 mM MgCl$_2$, 0.001% gelatin, 10 mM Tris, pH 8.3, 7.5–15 µCi$^{32}$P-CTP and 2 units of AmpliTaq (Perkin-Elmer Cetus) in a volume of 25 µl (Saiki et al. (1989) *Science* 239: 2766–2770). Samples were amplified for 30 cycles of 1 min at 94° C., 2 min at 62° C. for "intron 5" amplification and 65° C. for "intron 7" amplification and 3 min at 72° C., followed by 7 min at 72° C. 5 µl of this PCR mixture was digested with 10 units of Hae III (BRL) containing 1X React Buffer 2 (BRL) in 30 µl for 2 h.

In FIG. 1A, lanes 1 and 2, 2 µl of digested DNA was diluted to 10 µl 5% glycerol, 0.05% bromophenol blue (BPB) and 0.05% xylene cyanol (XC) and 5 µl was used per lane. For FIG. 1A, lanes 3 and 4, 2 µl of digested DNA was diluted with 8 µl 95% formamide, 10 mM NaOH, 0.05% BPB and 0.05% XC and incubated at 100° C. for 2 min and 5 µl was used per lane. For the remaining SSCP analyses, 1 µl of digested DNA was diluted with 19 µl 95% formamide, 10 mM NaOH, 0.05% BPB and 0.05% XC and incubated at 100° C. for 2 min. 7 µl of this denatured DNA was loaded per lane and electrophoresed on a 5% polyacrylamide gel using a sequencing gel apparatus (Orita et al. (1989) *Genomics* 5: 874–879). Electrophoresis was carried out at room temperature for 17.5 h at 200 V. The gels were dried and autoradiographed at −70° C.

b) Linkage Analysis

Data were entered into the programs provided by CEPH, and files with chromosome 11 markers were prepared using SETPED. Two point LOD score analyses were performed using MAPMAKER (Lander et al. (1987) *Genomics* 1: 174–181), and the two-point values were employed for multipoint analysis. By the linkage map of Junien and Van Heyningen (1991) *Cytogenet. Cell Genet.* 58: 459–554, TPH was located on the map with the TRY function of MAP-MAKER. All primary data have been contributed to CEPH and are freely available (Dausset et al. supra)

Results

To identify a polymorphism in the TPH gene, we performed single-strand conformational polymorphism (SSCP) analysis of TPH introns. The human TPH cDNA sequence (Boularand et al. (1990) *Nucl. Acids Res.* 18: 4257) was aligned with the mouse genomic TPH sequence (Stoll and Goldman (1991) *J. Neurosci. Res.* 28: 457–465) to identify intron locations in the human TPH gene and oligonucleotides were synthesized to amplify human introns corresponding to mouse intron 7.

When the region corresponding to intron 7 of the mouse TPH gene was amplified, a fragment of approximately 890 bp was amplified demonstrating the presence of an intron of approximately 830 bp. The amplified DNA was digested with Hae III to yield fragments of 500, 210 and 180 bp in which conformational variation can be more sensitively detected (FIG. 1,A, lanes 3 and 4). Although no polymorphism can be detected with native DNA (FIG. 1,a lanes 1 and 2), an SSCP polymorphism in the 210 bp fragment was observed using the SSCP technique of running the denatured DNA on a native gel (FIG. 1,A, lanes 3 and 4). Two allelic variants were identified and labeled U and L, as shown in FIG. 1. Allele frequencies were determined in 72 unrelated Caucasian individuals (CEPH parents) and the more common L allele had a frequency of 0.60.

The TPH alleles segregate in codominant Mendelian fashion, as can be seen in family 1423 in FIG. 1B. To genetically map the TPH gene to its chromosomal location, the polymorphism was typed in all 24 CEPH families which were informative. As cited above, TPH has been physically assigned by in situ hybridization to the chromosome region 11p15,3→p14 (Craig (1991) *Cytogenet. Cell Genet.* 56: 157–159). To place the gene on the linkage map, two-point and multipoint linkage analysis were performed.

FIG. 2 displays maximum LOD (log of the odds) scores with respect to other chromosome 11 markers. RFLP markers specific to closely linked loci was used to map the location of the TPH gene. Multipoint analysis with the closest markers places TPH centromeric to insulin, hemoglobin-$\beta$ (HBB) and D11S134. This places the TPH polymorphism at chromosomal region 11p155.

EXAMPLE II

This Example demonstrates that, in impulsive violent subjects, a polymorphism in the tryptophan hydroxylase (TPH) gene is correlated with 5-hydroxyindoleacetic acid (5-HIAA) concentration and also with a history of suicide attempts. The polymorphism is also significantly correlated with reduced fasting blood glucose concentrations. The strong relationship between TPH genotype and suicide attempts demonstrates that this type of impulsive behavior is influenced by genetic factors.

In the previous example, a polymorphic site in one of the introns of the human TPH gene was identified by single-strand conformational polymorphism analysis. Two alleles, referred to as the U and L alleles were identified and genetically mapped to chromosome 11 in close proximity to tyrosine hydroxylase. The L allele was found to be correlated with abnormal serotonergic behavior. Both alleles are quite common in Caucasians, with the U allele present at a frequency of 0.41.

Materials and Methods

We analyzed TPH genotype, CSF 5-HIAA concentration, blood glucose concentrations, and history of suicide attempts in a population of Finnish alcoholic violent offenders and arsonists who were classified as impulsive or non-impulsive based on the characteristics of their crimes. Impulsive crimes were committed without premeditation or provocation, whereas non-impulsive crimes were clearly premeditated. Finnish healthy volunteer subjects served as a control group. Many of the subjects in the impulsive group had very low concentrations of CSF 5-HIAA and thus represent an ideal population to search for linkage association to markers at genetic loci related to serotonergic function.

Subjects were interviewed and psychiatrically diagnosed using DSM-III criteria, confirming the division of the subjects into impulsive and non-impulsive subsets. Spitzer, supra. Of the impulsive group, 18 of 33 had antisocial personality disorder while the other 15 had intermittent explosive disorder. All offenders fulfilled criteria for alcohol abuse or dependence. All healthy volunteers were free of any mental disorders. CSF 5-HIAA concentrations, TPH genotypes, and blood glucose concentrations were determined blind to the results of the interviews. TPH genotype was determined in all subjects. CSF 5-HIAA and history of suicide attempts were available in 24 impulsive and 9 non-impulsive offenders, and in 27 healthy volunteers.

CSF was obtained by lumbar puncture and 5-HIAA concentrations were measured by HPLC as described by Scheinin et al. (1983) *Anal. Biochem.* 131: 246.

The fasting blood glucose concentrations were determined as follows. At 8:00 a.m., after a 12 hour overnight fast, the subjects consumed 1 g/kg of body weight (4 ml/kg) of glucose solution or an identical volume of an aspartame solution of indistinguishable sweetness (Leiras, Turku, Finland). Fifteen ml blood samples were drawn from an antecubital vein into an aprotinin-containing test tube (12.5 mIU/ml, ANTAGOSAN Behringwerke, Marburg, Germany) prior to, and 15, 30, 60, 90, 120, 180, 240, and 300 minutes after the administration of the liquid. For the first two hours of the test, the subjects rested in bed. Thereafter, they were allowed to move about on the ward, but resting was encouraged. All samples were assayed in duplicate. When the results of the duplicate determinations were discrepant by more than 5%, the samples were reanalyzed.

Results

Figure 3:
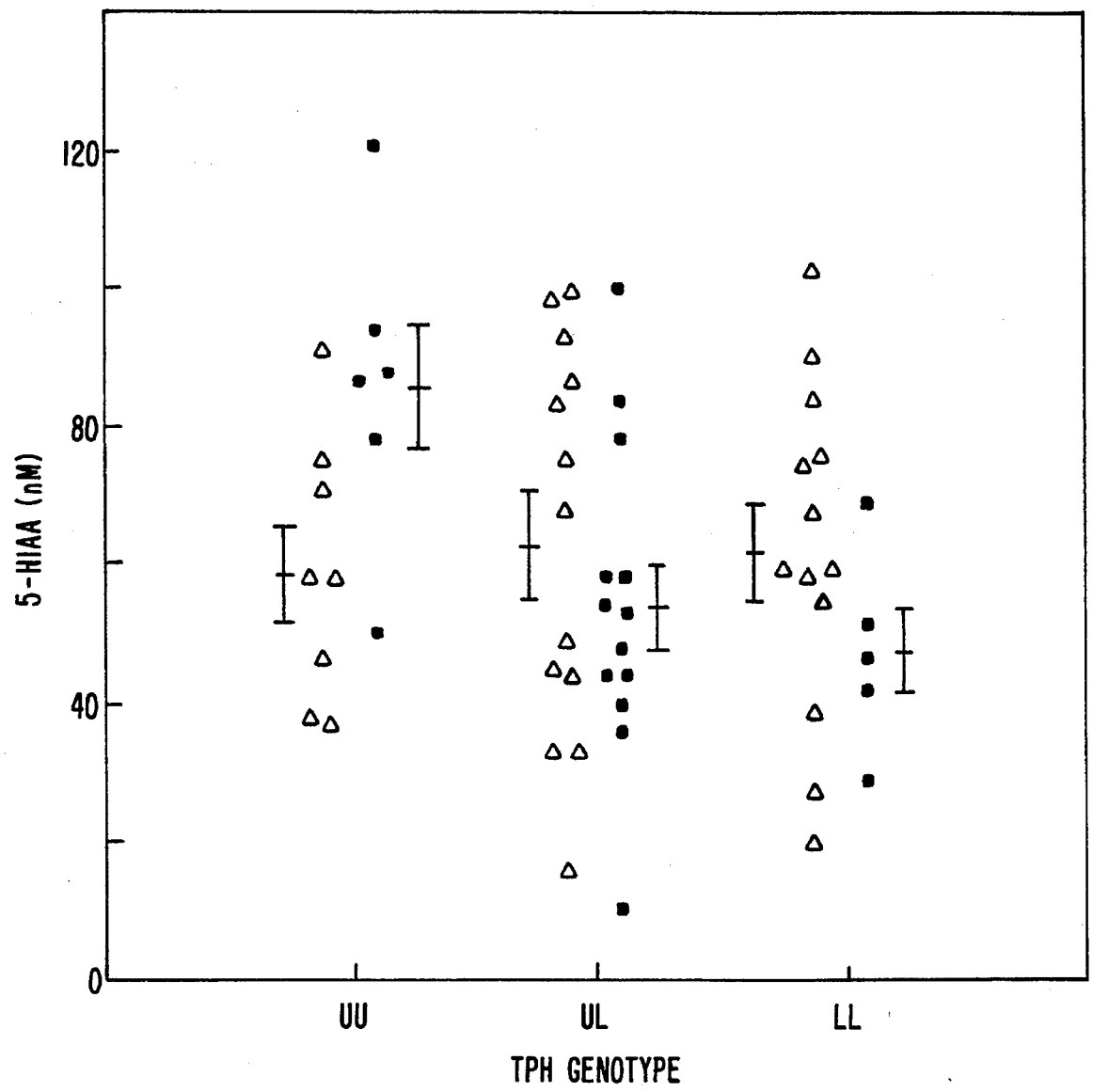
FIG. 3 shows the relationship between TPH genotype and 5-HIAA concentration. The 5-HIAA concentration of the subjects are plotted versus their TPH genotype. Non-impulsive subjects are represented with open triangles and impulsive subjects are represented with solid squares. Mean 5-HIAA concentration (±s.e.m) for each TPH genotype is shown.

A population association of tryptophan hydroxylase genotype to CSF 5-HIAA concentration is shown in Table 1. In this group of Finns, the U allele is present with a frequency of 0.45. Although no difference in the frequency of the TPH alleles between the impulsive and non-impulsive groups was observed, in the impulsive group there is a significant correlation of CSF 5-HIAA concentration with TPH genotype (FIG. 3 and Table 1). Among the impulsive offenders, the UU genotype group has the highest mean 5-HIAA concentration at 85 nM/ml, the UL group at 53 nM/ml and the LL group at 47 nM/ml. Hence, the U allele is associated with a higher TPH enzymatic activity than its L polymorphic counterpart in the impulsive subjects. Impulsive offenders with homozygous L alleles synthesize less serotonin than those with homozygous U alleles, while heterozygous UL impulsives tend to have a relatively low rate of serotonin synthesis.

TABLE 1

Population association of 5-HIAA concentration and TPH genotype in impulsive and non-impulsive Finns.

| | 5-HIAA (nM/ml) | | |
|---|---|---|---|
| Genotype | Impulsive | Non-Impulsive | Total |
| UU | 85 ± 9 (6) | 58 ± 7 (8) | 70 ± 6 (14) |
| UL | 53 ± 6 (13) | 62 ± 8 (13) | 58 ± 5 (26) |
| LL | 47 ± 6 (5) | 61 ± 7 (13) | 57 ± 5 (18) |
| | p = 0.011 | n.s | n.s. |
| 5-HIAA concentration: | 60 ± 5 (24) | 61 ± 4 (34) | 61 ± 3 (58) |
| Frequency of (UU): | 0.27 | 0.24 | 0.25 |
| U allele frequency: | 0.52 | 0.40 | 0.45 |

5-HIAA concentrations are presented as nM/ml ± s.e.m. with the number of subjects in parentheses. Probabilities were calculated by one-way ANOVAs.

Figure 4:
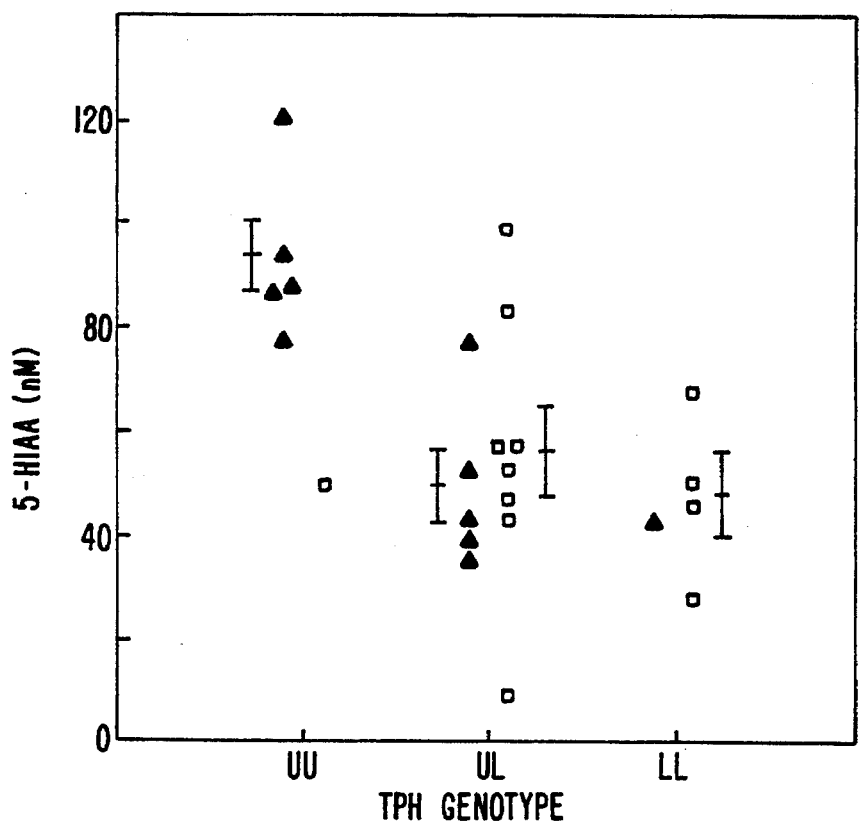
FIG. 4 shows the relationship between genotype, 5-HIAA concentration, and history of suicide attempts in impulsive subjects. The 5-HIAA concentrations for the impulsive subjects are plotted versus their TPH genotype. Subjects that have never attempted suicide (closed triangles), have attempted suicide (open squares), or have died from suicide (open squares with slash) are presented. Mean 5-HIAA concentration (±s.e.m) for each TPH genotype is shown.

As described in Table 2 and FIG. 4, there is a strong association of TPH genotype with a history of suicide attempts in the impulsive offenders. The U allele was present at a frequency of 0.70 in individuals who had never attempted suicide, but only 0.38 in those who had previously attempted suicide. Table 2 shows that only 17% of the UU impulsive subjects have attempted suicide while 62% of the impulsive offenders with the UL genotype and 80% of the LL genotypes have attempted suicide. Hence, among the impulsive offenders, the presence of one L allele is associated with a 4.0 fold increase in relative risk of attempted suicide. Furthermore, the only non-impulsive subject in this study who had attempted suicide had the LL genotype. 5-HIAA concentrations in the present sample correlate with suicidal behavior.

TABLE 2

Population association of suidide attempts with TPH genotypes and 5-HIAA concentration in impulsive violent Finns.

| | 5-HIAA (nM/ml) | | Frequency |
|---|---|---|---|
| Genotype | No Attempt | Attempted | of Attempted |
| UU | 93 ± 7 (5) | 49 (1) | 0.17 |
| UL | 49 ± 7 (5) | 56 ± 9 (8) | 0.64 |
| LL | 42 (1) | 48 ± 8 (4) | 0.80 |
| | p = 0.0067 | n.s | n.s. |
| 5-HIAA concentration: | 68 ± 8 (11) | 53 ± 6 (13) | |
| Frequency of (UU): | 0.45 | 0.08 | |
| U allele frequency: | 0.70 | 0.38 | |

5-HIAA concentrations are presented as nM/ml ± s.e.m. with the number of subjects in parentheses. Probabilities were calculated by one-way ANOVAs.

This study indicates that the genotyping of impulsive patients for this TPH polymorphism provides a predictive measure for risk of future suicide attempts.

Figure 5:
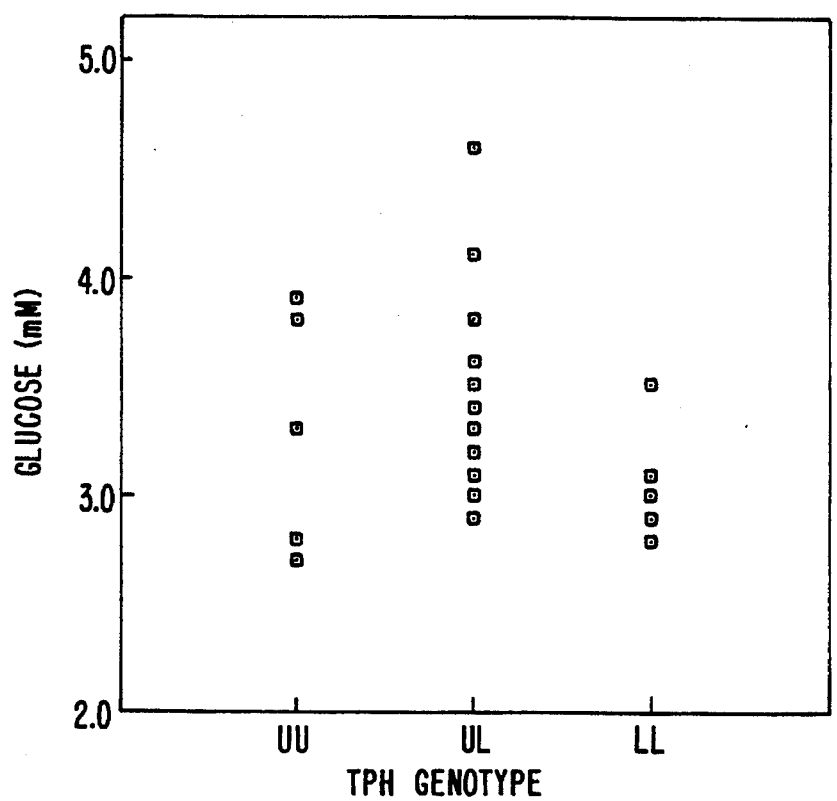
FIG. 5 shows the relationship between TPH genotype and fasting blood glucose concentrations.

Serotonin related conditions, for example, glucose metabolism, are also associated with the TPH polymorphism, (Table 3 and FIG. 5). When fasting blood glucose concentrations were measured and correlated with genotype in the alcoholic impulsive Finns, significantly lower glucose concentrations were found in subjects with the homozygous LL genotype. From this we can conclude that low serotonin biosynthesis causes reduced glucose concentrations. Anatomical links in the brain between the serotonergic system and regions regulating glucose metabolism and circadian rhythm are known (see, e.g., Moore et al., (1972) Brain Research 42: 201).

TABLE 3

Population association of blood glucose concentrations with TPH genotype in impulsive and non-impulsive violent Finns.

| | Blood glucose (mM) | |
|---|---|---|
| Genotype | Impulsive | Non-Impulsive |
| UU | 3.37 ± 0.18 (7) | 3.19 ± 0.17 (8) |
| UL | 3.50 ± 0.09 (18) | 3.45 ± 0.08 (15) |
| LL | 3.06 ± 0.08 (7) | 3.47 ± 0.09 (13) |
| | p = 0.053 | n.s. |

The lowest glucose concentrations at any of the indicated timepoints after aspartame administration are presented as mM (± s.e.m.) with the number of subjects in parentheses. Probabilities were calculated by one-way ANOVAs.

In conclusion, this example demonstrates that in impulsive subjects the TPH genotype is correlated with CSF 5-HIAA concentration which, in turn, may be indicative of altered CNS serotonin metabolism. Therefore, this genotypic difference in the control of serotonin biosynthesis is specifically associated with an increased probability to attempt suicide and with reduced glucose levels. This is the first study to implicate a specific gene in the predisposition to specific putative serotonergic behaviors.

EXAMPLE III

PCR probes known to flank the intron of the human TPH gene were synthesized by standard methods. Genomic DNA from individual patients was then PCR amplified using the PCR amplification methods described in Example I, herein. The PCR-amplified DNA was then isolated and sequenced using standard techniques. (See Sambrook, et al., supra.) The DNA sequence of the intron and short exon regions sequence regions of the two exons flanking the intron for both the U and L alleles is shown in FIG. 6. Two point mutations in the intron at positions number 317 and 878 in FIG. 6 were identified in the L allele.

Without wishing to be bound by theory, the point mutations located in the L allele of the TPH gene intron shown in FIG. 6 may cause production of an aberrant TPH mRNA. Specifically, the point mutations found in the intron may direct aberrant splicing of the TPH pre-mRNA. Correct splicing requires the recognition of the 5' donor site. A lariat structure is formed when the donor site is transesterified to the branch point. Scanning then occurs to the first AG in the sequence after a polypyrimidine tract. Potential branch point sequences in the TPH intron are found in FIG. 6 at nucleotide 809–815 (TTTCGAT), 826–832 (CGTTGAT) and 857–863 (GCGTGAC). These sequence regions fit the loosely defined consensus sequence YNYTRAY at 6 of 7 bases. (See Fu, X-Y, et al. (1988), *EMBO J.* 7:809–817 and Smith, C. W. J., et al. (1993) *Mol. Cell. Biol.* 13:4939–4952.) Scanning to the 3' acceptor site probably starts in the polypyrimidine tract CCTCTCTTTC (Seq. ID No.:5) located at bases 873–882. The first YAG (base 882–884) encountered is the 3' acceptor site. The mutation in the L alleles at base 317 may activate a cryptic slice site by creating a new polypyrimidine-rich sequence TGCTAGCTSCTATTCT (base 306–330) just downstream of a potential branch point TATTAAT at bases 293–299. Scanning to the first YAG (bases 332–333) with subsequent splicing would thus produce an aberrant mRNA, which in turn would cause production of an aberrant TPH protein, thereby affecting serotonin metabolism.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A method of detecting abnormal serotonergic function in an impulsive human subject, the method comprising:
   providing a nucleic acid sample from the human subject;
   detecting the presence or absence of an L allele of the gene encoding tryptophan hydroxylase in the sample, wherein detecting the presence of the L allele detects abnormal serotonergic function in the impulsive human subject.

2. The method of claim 1, wherein the L allele is in a homozygous state.

3. The method of claim 1 wherein the L allele is detected using a polymerase chain reaction.

4. The method of claim 3 wherein the polymerase chain reaction uses primers that hybridize to the same nucleic acid sequence as an oligonucleotide selected from the group that consists of:

HTHSSCP4: 5'-TTCAGATCCCTTCTATACCCCA-GAG-3' (Seq. ID No.:3)

HTHSSCP5: 5'-GGACATGACCTAAGAGTTCATG-GCA-3' (Seq. ID No.:4).

5. The method of claim 1 wherein the L allele is detected by single strand conformation polymorphism analysis.

6. The method of claim 1 wherein the L allele is associated with a polymorphism within an intron of the gene encoding tryptophan hydroxylase.

7. The method of claim 6 wherein the intron corresponds to intron 7 of the mouse gene encoding tryptophan hydroxylase.

8. The method of claim 1 wherein the abnormal serotonergic function is suicidal behavior.

9. The method of claim 7 wherein the polymorphism is correlated with suicidal behavior.

10. An isolated nucleic acid consisting of a subsequence of the L allele of the gene encoding tryptophan hydroxylase, wherein the subsequence is SEQ. ID No:8.

11. The nucleic acid of claim 10 wherein the nucleic acid is obtained by polymerase chain reaction amplification of a nucleic acid sample from an impulsive subject.

12. A nucleic acid of claim 10 wherein the subsequence of the L allele comprises an intron.

13. A nucleic acid of claim 12 wherein the intron corresponds to intron 7 of the mouse gene encoding tryptophan hydroxylase.

* * * * *